United States Patent
Maiyuran et al.

(10) Patent No.: US 8,377,693 B2
(45) Date of Patent: Feb. 19, 2013

(54) POLYPEPTIDES HAVING CELLOBIOHYDROLASE ACTIVITY AND POLYNUCLEOTIDES ENCODING SAME

(75) Inventors: Suchindra Maiyuran, Gold River, CA (US); Paul Harris, Carnation, WA (US); Hanshu Ding, Davis, CA (US); Kimberly Brown, Elk Grove, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/548,706

(22) Filed: Jul. 13, 2012

(65) Prior Publication Data

US 2012/0276640 A1    Nov. 1, 2012

Related U.S. Application Data

(62) Division of application No. 13/405,988, filed on Feb. 27, 2012, now Pat. No. 8,227,667, which is a division of application No. 12/680,433, filed as application No. PCT/US2008/077864 on Sep. 26, 2008, now Pat. No. 8,124,394.

(60) Provisional application No. 60/976,207, filed on Sep. 28, 2007.

(51) Int. Cl.
*C12N 1/00* (2006.01)
*C12N 15/79* (2006.01)

(52) U.S. Cl. .................. 435/471; 435/254.11; 536/23.2
(58) Field of Classification Search .................. None
See application file for complete search history.

(56) References Cited

U.S. PATENT DOCUMENTS

| 7,883,872 B2 | 2/2011 | Gusakov et al. |
| 7,923,236 B2 | 4/2011 | Gusakov et al. |
| 2007/0238155 A1 | 10/2007 | Gusakov et al. |

FOREIGN PATENT DOCUMENTS

| WO | WO 2004/056981 | 7/2004 |
| WO | WO 2006/074435 | 7/2006 |

OTHER PUBLICATIONS

Gusakov et al., 2007, Design of Highly Efficient Cellulase Mixtures for Enzymatic Hydrolysis of Cellulose, *Biotechnology Bioengineering* 97: 1028-1038.
Guskov et al, Jan. 24, 2008, Geneseq, Access No. ALK33729.

*Primary Examiner* — Nashaat Nashed
(74) *Attorney, Agent, or Firm* — Robert L Starnes

(57) ABSTRACT

The present invention relates to isolated polypeptides having cellobiohydrolase activity and isolated polynucleotides encoding the polypeptides. The invention also relates to nucleic acid constructs, vectors, and host cells comprising the polynucleotides as well as methods of producing and using the polypeptides.

8 Claims, 4 Drawing Sheets

POLYPEPTIDES HAVING CELLOBIOHYDROLASE ACTIVITY AND POLYNUCLEOTIDES ENCODING SAME

CROSS-REFERENCE TO RELATED APPLICATIONS

This application is a divisional of U.S. application Ser. No. 13/405,988 filed on Feb. 27, 2012, which is a divisional of U.S. application Ser. No. 12/680,433 filed on Mar. 26, 2010, now U.S. Pat. No. 8,124,394, which is a 35 U.S.C. §371 national application of PCT/US2008/077864 filed on Sep. 26, 2008 and claims priority from U.S. Provisional Application No. 60/976,207 filed on Sep. 28, 2007, which applications are incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having cellobiohydrolase activity and isolated polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose can be easily fermented by yeast into ethanol.

WO 2004/056981 discloses cellobiohydrolases from *Chaetomium thermophilum* and *Myceliophthora thermophila*. Gusakov et al., 2007, *Biotechnology Bioengineering* 97: 1028-1038, describe a cellobiohydrolase isolated from *Chrysosporium lucknowense*.

The present invention relates to polypeptides having cellobiohydrolase activity and polynucleotides encoding the polypeptides.

SUMMARY OF THE INVENTION

The present invention relates to isolated polypeptides having cellobiohydrolase activity selected from the group consisting of:

(a) a polypeptide comprising an amino acid sequence having at least 80% identity to the mature polypeptide of SEQ ID NO: 2;

(b) a polypeptide encoded by a polynucleotide that hybridizes under at least high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polypeptide encoded by a polynucleotide comprising a nucleotide sequence having at least 80% identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having cellobiohydrolase activity, selected from the group consisting of:

(a) a polynucleotide encoding a polypeptide comprising an amino acid sequence having at least 80% identity to the mature polypeptide of SEQ ID NO: 2;

(b) a polynucleotide that hybridizes under at least high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polynucleotide comprising a nucleotide sequence having at least 80% identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing a polypeptide having cellobiohydrolase activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods of using the polypeptides having cellobiohydrolase in detergents and in the conversion of cellulose to glucose and various substances.

The present invention also relates to plants comprising an isolated polynucleotide encoding such a polypeptide having cellobiohydrolase activity.

The present invention also relates to methods of producing such a polypeptide having cellobiohydrolase, comprising: (a) cultivating a transgenic plant or a plant cell comprising a polynucleotide encoding such a polypeptide having cellobiohydrolase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 17 of SEQ ID NO: 2, wherein the gene is foreign to the nucleotide sequence.

BRIEF DESCRIPTION OF THE FIGURES

FIGS. 1A and 1B show the genomic DNA sequence and the deduced amino acid sequence of a *Myceliophthora thermophila* CBS 202.75 cellobiohydrolase (SEQ ID NOs: 1 and 2, respectively).

DEFINITIONS

Figure 2:
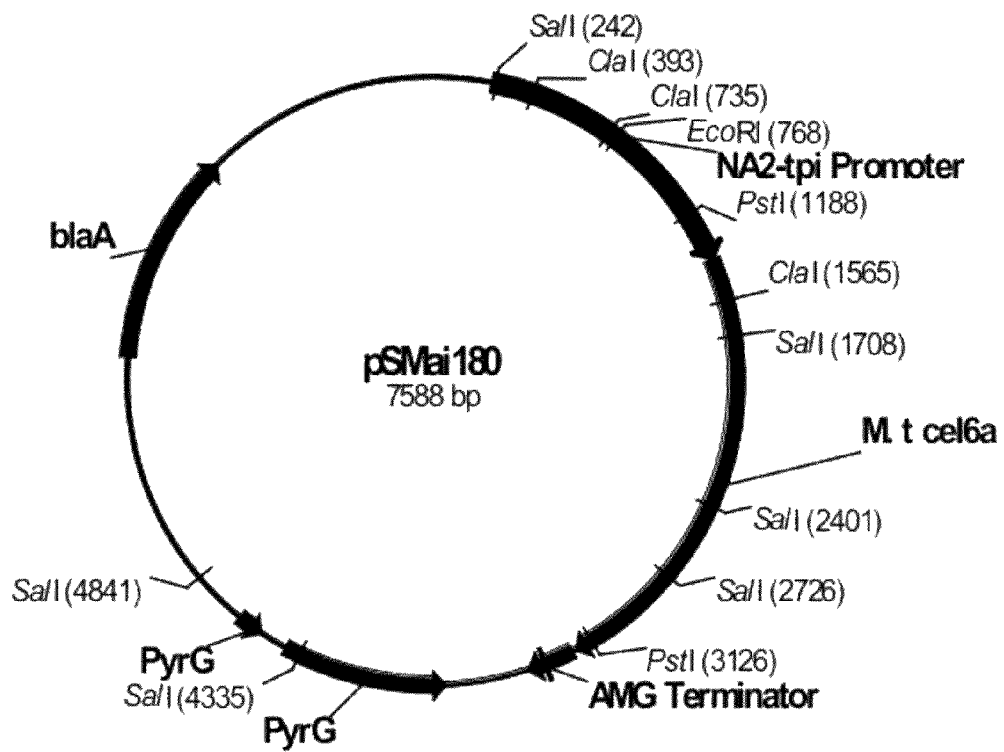
FIG. 2 shows a restriction map of pSMai180.
Figure 3:
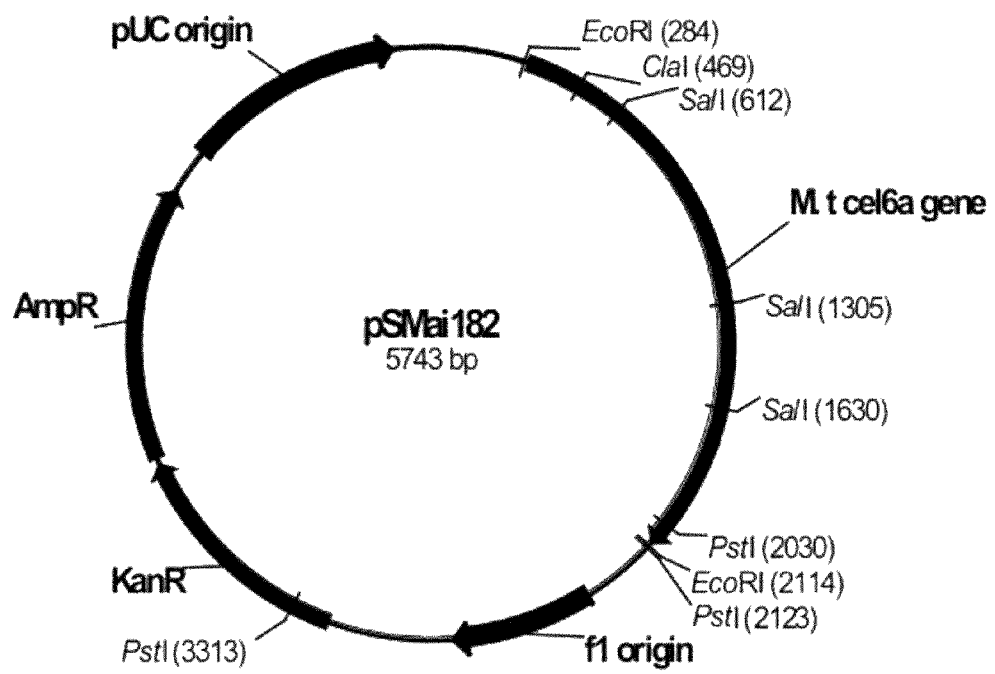
FIG. 3 shows a restriction map of pSMai182.

Cellobiohydrolase activity: The term "cellobiohydrolase activity" is defined herein as a 1,4-D-glucan cellobiohydrolase (E.C. 3.2.1.91) activity that catalyzes the hydrolysis of 1,4-beta-D-glucosidic linkages in cellulose, cellotetriose, or any beta-1,4-linked glucose containing polymer, releasing cellobiose from the reducing or non-reducing end of the chain. For purposes of the present invention, cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine cellobiohydrolase activity on a fluorescent disaccharide derivative.

Endoglucanase activity: The term "endoglucanase activity" is defined herein as an endo-1,4-(1,3;1,4)-beta-D-glucan 4-glucanohydrolase (E.C. 3.2.1.4) that catalyses endohydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

Beta-glucosidase activity: The term "beta-glucosidase activity" is defined herein as a beta-D-glucoside glucohydrolase (E.C. 3.2.1.21) activity that catalyzes the hydrolysis of terminal non-reducing beta-D-glucose residues with the release of beta-D-glucose. Cellobiase is synonymous with beta-glucosidase. For purposes of the present invention, beta-glucosidase activity is determined at 25° C. using 1 mM 4-nitrophenyl-beta-D-glucopyranoside as substrate in 50 mM sodium citrate pH 4.8. One unit of beta-glucosidase activity is defined as 1.0 pmole of 4-nitrophenol produced per minute at 25° C., pH 4.8.

Family 6 or Family GH6 or Cel6: The term "Family 6" or "Family GH6" or "Cel6" is defined herein as a polypeptide falling into the glycoside hydrolase Family 6 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. According to such a classification, SEQ ID NO: 2 or the mature polypeptide thereof belongs to Family 6 and is predicted to be a cellobiohydrolase II.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having cellobiohydrolase activity that is in its final form following translation and any post-translational modifications, such as N-terminal processing, C-terminal truncation, glycosylation, phosphorylation, etc. In a preferred aspect, the mature polypeptide is amino acids 18 to 482 of SEQ ID NO: 2 based on the SignalP software program (Nielsen et al., 1997, *Protein Engineering* 10: 1-6) that predicts amino acids 1 to 17 of SEQ ID NO: 2 are a signal peptide.

Mature polypeptide coding sequence: The term "mature polypeptide coding sequence" is defined herein as a nucleotide sequence that encodes a mature polypeptide having cellobiohydrolase activity. In a preferred aspect, the mature polypeptide coding sequence is nucleotides 52 to 1809 of SEQ ID NO: 1 based on the SignalP software program (Nielsen et al., 1997, *Protein Engineering* 10:1-6) that predicts nucleotides 1 to 51 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Myceliophthora thermophila* cellobiohydrolase of SEQ ID NO: 2 or the mature polypeptide thereof.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has cellobiohydrolase activity. In a preferred aspect, a fragment contains at least 415 amino acid residues, more preferably at least 435 amino acid residues, and most preferably at least 455 amino acid residues, of the mature polypeptide of SEQ ID NO: 2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having cellobiohydrolase activity. In a preferred aspect, a subsequence contains at least 1245 nucleotides, more preferably at least 1305 nucleotides, and most preferably at least 1365 nucleotides of the mature polypeptide coding sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having cellobiohydrolase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Cellobiohydrolase Activity

In a first aspect, the present invention relates to isolated polypeptides comprising an amino acid sequence having a degree of identity to the mature polypeptide of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have cellobiohydrolase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having cellobiohydrolase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 18 to 482 of SEQ ID NO: 2, or an allelic variant thereof; or a fragment thereof having cellobiohydrolase activity. In another preferred aspect, the polypeptide comprises amino acids 18 to 482 of SEQ ID NO: 2. In another preferred aspect, the polypeptide consists of the amino acid sequence of SEQ ID NO: 2 or an allelic variant thereof; or a fragment thereof having cellobiohydrolase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 18 to 482 of SEQ ID NO: 2 or an allelic variant thereof; or a fragment thereof having cellobiohydrolase activity. In another preferred aspect, the polypeptide consists of amino acids 18 to 482 of SEQ ID NO: 2.

In a second aspect, the present invention relates to isolated polypeptides having cellobiohydrolase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having cellobiohydrolase activity. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having cellobiohydrolase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may, therefore, be screened for DNA that hybridizes with the probes described above and encodes a polypeptide having cellobiohydrolase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the cDNA sequence contained in the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 52 to 1809 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pSMai182 which is contained in *E. coli* NRRL B-50059, wherein the polynucleotide sequence thereof encodes a polypeptide having cellobiohydrolase activity. In another preferred aspect, the nucleic acid probe is the mature polypeptide coding region contained in plasmid pSMai182 which is contained in *E. coli* NRRL B-50059.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having cellobiohydrolase activity encoded by polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., cellobiohydrolase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 18 to 482 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides Having Cellobiohydrolase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having cellobiohydrolase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having cellobiohydrolase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having cellobiohydrolase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having cellobiohydrolase activity.

In another preferred aspect, the polypeptide is a *Streptococcus equisimilis, Streptococcus pyogenes, Streptococcus uberis,* or *Streptococcus equi* subsp. *Zooepidemicus* polypeptide having cellobiohydrolase activity.

In another preferred aspect, the polypeptide is a *Streptomyces achromogenes, Streptomyces avermitilis, Streptomyces coelicolor, Streptomyces griseus,* or *Streptomyces lividans* polypeptide having cellobiohydrolase activity.

A polypeptide having cellobiohydrolase activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having cellobiohydrolase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having cellobiohydrolase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellobiohydrolase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having cellobiohydrolase activity.

In another preferred aspect, the polypeptide is a *Myceliophthora thermophila, Myceliophthora fergusii, Myceliophthora hinnulea, Myceliophthora histoplasmoides, Myceliophthora indica, Myceliophthora lutea, Myceliophthora sulphurea, Myceliophthora thermophila,* or *Myceliophthora vellerea* polypeptide.

In a more preferred aspect, the polypeptide is a *Myceliophthora thermophila* polypeptide having cellobiohydrolase activity. In a most preferred aspect, the polypeptide is a *Myceliophthora thermophila* CBS 202.75 polypeptide having cellobiohydrolase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having cellobiohydrolase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having cellobiohydrolase activity of the present invention.

In a preferred aspect, the nucleotide sequence comprises or consists of SEQ ID NO: 1. In another more preferred aspect, the nucleotide sequence comprises or consists of the sequence contained in plasmid pSMai182 which is contained in *E. coli* NRRL B-50059. In another preferred aspect, the nucleotide sequence comprises or consists of the mature polypeptide coding sequence of SEQ ID NO: 1. In another preferred aspect, the nucleotide sequence comprises or consists of nucleotides 52 to 1809 of SEQ ID NO: 1. In another more preferred aspect, the nucleotide sequence comprises or consists of the mature polypeptide coding sequence contained in plasmid pSMai182 which is contained in *E. coli* NRRL B-50059. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have cellobiohydrolase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Myceliophthora*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for cellobiohydrolase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); and (b) isolating the hybridizing polynucleotide, which encodes a polypeptide having cellobiohydrolase activity. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137. Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 17 of SEQ ID NO: 2. In another preferred aspect, the signal peptide coding sequence comprises or consists of nucleotides 1 to 51 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus*. Gram negative bacteria include, but not limited to, *E. coli,*

*Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis,* and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum,*

*Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Myceliophthora*. In a more preferred aspect, the cell is *Myceliophthora thermophila*. In a most preferred aspect, the cell is *Myceliophthora thermophila* CBS 202.75.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having cellobiohydrolase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, gPlant Molecular Biology 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having cellobiohydrolase activity of the present invention under conditions conducive for production of the polypeptide; and (b) recovering the polypeptide.

Removal or Reduction of Cellobiohydrolase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of cellobiohydrolase activity by fermentation of a cell that produces both a polypeptide of the present invention as well as the protein product of interest by adding an effective amount of an agent capable of inhibiting cellobiohydrolase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of cellobiohydrolase activity by cultivating the cell under conditions permitting the expression of the product, subjecting the resultant culture broth to a combined pH and temperature treatment so as to reduce the cellobiohydrolase activity substantially, and recovering the product from the culture broth. Alternatively, the combined pH and temperature treatment may be performed on an enzyme preparation recovered from the culture broth. The combined pH and temperature treatment may optionally be used in combination with a treatment with a cellobiohydrolase Inhibitor.

In accordance with this aspect of the invention, it is possible to remove at least 60%, preferably at least 75%, more preferably at least 85%, still more preferably at least 95%, and most preferably at least 99% of the cellobiohydrolase activity. Complete removal of cellobiohydrolase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially cellobiohydrolase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The cellobiohydrolase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellobiohydrolase activity that is produced by a method of the present invention.

Methods of Inhibiting Expression of a Polypeptide Having Cellobiohydrolase Activity The present invention also relates to methods of inhibiting the expression of a polypeptide having cellobiohydrolase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in viva In one aspect, the dsRNA molecules can be used to generate a loss-of-function mutation in a cell, an organ or an animal. Methods for making and using dsRNA molecules to selectively degrade RNA are well known in the art, see, for example, U.S. Pat. Nos. 6,506,559; 6,511,824; 6,515,109; and 6,489,127.

Compositions

The present invention also relates to compositions comprising a polypeptide of the present invention. Preferably, the compositions are enriched in such a polypeptide. The term "enriched" indicates that the cellobiohydrolase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus Aspergillus, preferably Aspergillus aculeatus, Aspergillus awamori, Aspergillus fumigatus, Aspergillus foetidus, Aspergillus japonicus, Aspergillus nidulans, Aspergillus niger, or Aspergillus oryzae; Fusarium, preferably Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides, or Fusarium venenatum; Humicola, preferably Humicola insolens or Humicola lanuginosa; or Trichoderma, preferably Trichoderma harzianum, Trichoderma koningii, Trichoderma longibrachiatum, Trichoderma reesei, or Trichoderma viride.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having cellobiohydrolase activity, or compositions thereof, as described below.

Degradation or Conversion of Cellulosic Material

The present invention also relates to methods for degrading or converting a cellulosic material, comprising: treating the cellulosic material with a composition comprising one or more cellulolytic proteins in the presence of an effective amount of a polypeptide having cellobiohydrolase activity of the present invention. In a preferred aspect, the method further comprises recovering the degraded or converted cellulosic material.

The polypeptides and host cells of the present invention may be used in the production of monosaccharides, disaccharides, and polysaccharides as chemical or fermentation feedstocks from cellulosic biomass for the production of ethanol, plastics, other products or intermediates. The composition comprising the polypeptide having cellobiohydrolase activity may be in the form of a crude fermentation broth with or without the cells removed or in the form of a semi-purified or purified enzyme preparation. The composition can also comprise other proteins and enzymes useful in the processing of biomass, e.g., endoglucanase, cellobiohydrolase, beta-glucosidase, hemicellulolytic enzymes, enhancers (WO 2005/074647, WO 2005/074656), etc. Alternatively, the composition may comprise a host cell of the present invention as a source of the polypeptide having cellobiohydrolase activity in a fermentation process with the biomass. In particular, the polypeptides and host cells of the present invention may be used to increase the value of processing residues (dried distillers grain, spent grains from brewing, sugarcane bagasse, etc.) by partial or complete degradation of cellulose or hemicellulose. The host cell may also contain native or heterologous genes that encode other proteins and enzymes, mentioned above, useful in the processing of biomass.

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

In the methods of the present invention, the cellulosic material can be any material containing cellulose. Cellulose is generally found, for example, in the stems, leaves, hulls, husks, and cobs of plants or leaves, branches, and wood of trees. The cellulosic material can be, but is not limited to, herbaceous material, agricultural residues, forestry residues, municipal solid wastes, waste paper, and pulp and paper mill residues. The cellulosic material can be any type of biomass including, but not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix.

In a preferred aspect, the cellulosic material is corn stover. In another preferred aspect, the cellulosic material is corn fiber. In another preferred aspect, the cellulosic material is corn cob. In another preferred aspect, the cellulosic material is rice straw. In another preferred aspect, the cellulosic material is paper and pulp processing waste. In another preferred aspect, the cellulosic material is woody or herbaceous plants. In another preferred aspect, the cellulosic material is bagasse. In another preferred aspect, the cellulosic material is orange peel.

Three major classes of enzymes are used to breakdown cellulosic biomass:
(1) The "endo-1,4-beta-glucanases" or 1,4-beta-D-glucan-4-glucanohydrolases (EC 3.2.1.4), which act randomly on soluble and insoluble 1,4-beta-glucan substrates.
(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.
(3) The "beta-D-glucosidases" or beta-D-glucoside glucohydrolases (EC 3.2.1.21), which act to release D-glucose units from cellobiose and soluble cellodextrins, as well as an array of glycosides.

The polypeptides having cellobiohydrolase activity of the present invention are preferably used in conjunction with other cellulolytic proteins, e.g., endo-1,4-beta-glucanase and exo-1,4-beta-D-glucanases, to degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

The endo-1,4-beta-glucanase and exo-1,4-beta-D-glucanases may be produced by any known method known in the art (see, e.g., Bennett, J. W. and LaSure, L. (eds.), *More Gene Manipulations in Fungi*, Academic Press, CA, 1991).

The optimum amounts of a polypeptide having cellobiohydrolase activity and other cellulolytic proteins depends on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation). The term "cellulolytic proteins" is defined herein as those proteins or mixtures of proteins shown as being capable of hydrolyzing or converting or degrading cellulose under the conditions tested.

In a preferred aspect, the amount of polypeptide having cellobiohydrolase activity per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

In another preferred aspect, the amount of cellulolytic proteins per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

In the methods of the present invention, the composition may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes may be derived or obtained from any suitable origin, including, bacterial, fungal, yeast or mammalian origin. The term "obtained" means herein that the enzyme may have been isolated from an organism which naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids which are deleted, inserted and/or substituted, i.e., a recombinantly produced enzyme which is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be substantially pure.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106, 991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

The methods of the present invention may be used to process a cellulosic material to many useful organic products, chemicals and fuels. In addition to ethanol, some commodity and specialty chemicals that can be produced from cellulose include xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., 1999, *Biocommodity Engineering, Biotechnol. Prog.*, 15: 777-793; Philippidis, G. P., 1996, Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the cellulosic material in accordance with the methods of the present invention are well understood to those skilled in the art. The methods of the present invention may be implemented using any conventional biomass processing apparatus configured to operate in accordance with the invention.

Such an apparatus may include a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol is combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

The present invention further relates to methods of producing a substance, comprising: (a) saccharifying a cellulosic material with an effective amount of a composition comprising one or more cellulolytic proteins in the presence of an effective amount of a polypeptide having cellobiohydrolase activity of the present invention; (b) fermenting the saccharified cellulosic material of step (a) with one or more fermentating microorganisms; and (c) recovering the substance from the fermentation. The composition comprising the polypeptide having cellobiohydrolase activity may be in the form of a crude fermentation broth with or without the cells removed or in the form of a semi-purified or purified enzyme preparation or the composition may comprise a host cell of the present invention as a source of the polypeptide having cellobiohydrolase activity in a fermentation process with the biomass.

The substance can be any substance derived from the fermentation. In a preferred embodiment, the substance is an alcohol. It will be understood that the term "alcohol" encompasses a substance that contains one or more hydroxyl moieties. In a more preferred embodiment, the alcohol is arabinitol. In another more preferred embodiment, the alcohol is butanol. In another more preferred embodiment, the alcohol is ethanol. In another more preferred embodiment, the alcohol is glycerol. In another more preferred embodiment, the alcohol is methanol. In another more preferred embodiment, the alcohol is 1,3-propanediol. In another more preferred embodiment, the alcohol is sorbitol. In another more preferred embodiment, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241;

Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred embodiment, the substance is an organic acid. In another more preferred embodiment, the organic acid is acetic acid. In another more preferred embodiment, the organic acid is acetonic acid. In another more preferred embodiment, the organic acid is adipic acid. In another more preferred embodiment, the organic acid is ascorbic acid. In another more preferred embodiment, the organic acid is citric acid. In another more preferred embodiment, the organic acid is 2,5-diketo-D-gluconic acid. In another more preferred embodiment, the organic acid is formic acid. In another more preferred embodiment, the organic acid is fumaric acid. In another more preferred embodiment, the organic acid is glucaric acid. In another more preferred embodiment, the organic acid is gluconic acid. In another more preferred embodiment, the organic acid is glucuronic acid. In another more preferred embodiment, the organic acid is glutaric acid. In another preferred embodiment, the organic acid is 3-hydroxypropionic acid. In another more preferred embodiment, the organic acid is itaconic acid. In another more preferred embodiment, the organic acid is lactic acid. In another more preferred embodiment, the organic acid is malic acid. In another more preferred embodiment, the organic acid is malonic acid. In another more preferred embodiment, the organic acid is oxalic acid. In another more preferred embodiment, the organic acid is propionic acid. In another more preferred embodiment, the organic acid is succinic acid. In another more preferred embodiment, the organic acid is xylonic acid. See, for example, Chen, R., and Lee, Y.Y., 1997, Membrane-mediated extractive fermentation for lactic acid production from cellulosic biomass, *Appl. Biochem. Biotechnol.* 63-65: 435-448.

In another preferred embodiment, the substance is a ketone. It will be understood that the term "ketone" encompasses a substance that contains one or more ketone moieties. In another more preferred embodiment, the ketone is acetone. See, for example, Qureshi and Blaschek, 2003, supra.

In another preferred embodiment, the substance is an amino acid. In another more preferred embodiment, the organic acid is aspartic acid. In another more preferred embodiment, the amino acid is glutamic acid. In another more preferred embodiment, the amino acid is glycine. In another more preferred embodiment, the amino acid is lysine. In another more preferred embodiment, the amino acid is serine. In another more preferred embodiment, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred embodiment, the substance is a gas. In another more preferred embodiment, the gas is methane. In another more preferred embodiment, the gas is $H_2$. In another more preferred embodiment, the gas is $CO_2$. In another more preferred embodiment, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy,* Vol. 13 (1-2), pp. 83-114, 1997, Anaerobic digestion of biomass for methane production: A review.

Production of a substance from cellulosic material typically requires four major steps. These four steps are pretreatment, enzymatic hydrolysis, fermentation, and recovery. Exemplified below is a process for producing ethanol, but it will be understood that similar processes can be used to produce other substances, for example, the substances described above.

Pretreatment. In the pretreatment or pre-hydrolysis step, the cellulosic material is heated to break down the lignin and carbohydrate structure, solubilize most of the hemicellulose, and make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730).

Saccharification. In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation. In the fermentation step, sugars, released from the cellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable cellulosic substrate or raw material may be used in a fermentation process of the present invention. The substrate is generally selected based on the desired fermentation product, i.e., the substance to be obtained from the fermentation, and the process employed, as is well known in the art. Examples of substrates suitable for use in the methods of present invention include cellulose-containing materials, such as wood or plant residues or low molecular sugars DP1-3 obtained from processed cellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Saccharomyces* spp., and in particular, *Saccharomyces cerevisiae*. Commercially available yeast include, e.g., RED STAR®/Lesaffre Ethanol Red (available from Red Star/Lesaffre, USA) FALI (available from Fleischmann's Yeast, a division of Burns Philp Food Inc., USA), SUPERSTART® (available from Alltech), GERT STRAND® (available from Gert Strand AB, Sweden) and FERMIOL® (available from DSM Specialties).

In a preferred embodiment, the yeast is a *Saccharomyces* spp. In a more preferred embodiment, the yeast is *Saccharomyces cerevisiae*. In another more preferred embodiment, the yeast is *Saccharomyces distaticus*. In another more preferred embodiment, the yeast is *Saccharomyces uvarum*. In another preferred embodiment, the yeast is a *Kluyveromyces*. In another more preferred embodiment, the yeast is *Kluyveromyces marxianus*. In another more preferred embodiment, the yeast is *Kluyveromyces fragilis*. In another preferred embodiment, the yeast is a *Candida*. In another more preferred embodiment, the yeast is *Candida pseudotropicalis*. In another more preferred embodiment, the yeast is *Candida brassicae*. In another preferred embodiment, the yeast is a *Clavispora*. In another more preferred embodiment, the yeast is *Clavispora lusitaniae*. In another more preferred embodiment, the yeast is *Clavispora opuntiae*. In another preferred embodiment, the yeast is a *Pachysolen*. In another more preferred embodiment, the yeast is *Pachysolen tannophilus*. In another preferred embodiment, the yeast is a *Bretannomyces*. In another more preferred embodiment, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example, *Zymomonas mobilis* and *Clostridium thermocellum* (Philippidis, 1996, supra).

It is well known in the art that the organisms described above can also be used to produce other substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae*, Appl. Biochem. Biotechnol. 39-40: 135-147; Ho, N. W. Y., Chen, Z, Brainard, A. P., 1998, Genetically engineered *Saccharomyces* yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis*, *Science* 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol.* 62: 4465-4470) has led to the construction of organisms capable of converting hexoses and pentoses to ethanol (cofermentation).

Yeast or another microorganism typically is added to the degraded cellulose or hydrolysate and the fermentation is ongoing for about 24 to about 96 hours, such as about 35 to about 60 hours. The temperature is typically between about 26° C. to about 40° C., in particular at about 32° C., and at about pH 3 to about pH 6, in particular around pH 4-5.

In a preferred embodiment, yeast or another microorganism is applied to the degraded cellulose or hydrolysate and the fermentation is ongoing for about 24 to about 96 hours, such as typically 35-60 hours. In a preferred embodiments, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5 \times 10^7$ viable count per ml of fermentation broth. During an ethanol producing phase the yeast cell count should preferably be in the range from approximately $10^7$ to $10^{10}$, especially around approximately $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol; drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Recovery. The alcohol is separated from the fermented cellulosic material and purified by conventional methods of distillation. Ethanol with a purity of up to about 96 vol. % ethanol can be obtained, which can be used as, for example, fuel ethanol, drinking ethanol, i.e., potable neutral spirits, or industrial ethanol.

For other substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

In the methods of the present invention, the polypeptide having cellobiohydrolase activity and other cellulolytic protein(s) may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

Detergent Compositions

The present invention also relates to detergent compositions, comprising a surfactant and a polypeptide having cellobiohydrolase activity of the present invention. The polypeptides having cellobiohydrolase activity may be added to and thus become a component of a detergent composition.

The detergent composition of the present invention may be, for example, formulated as a hand or machine laundry detergent composition including a laundry additive composition suitable for pre-treatment of stained fabrics and a rinse added fabric softener composition, or formulated as a detergent composition for use in general household hard surface cleaning operations, or formulated for hand or machine dishwashing operations.

In a specific aspect, the present invention provides a detergent additive comprising the polypeptides having cellobiohydrolase activity of the present invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the enzymatic components should be compatible with the selected detergent, (i.e., pH-optimum, compatibility with other enzymatic and non-enzymatic ingredients, etc.), and the enzymatic components should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE™, SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g., from H. lanuginosa (T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al., 1993, Biochemica et Biophysica Acta, 1131, 253-360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipases include LIPOLASE™, LIPEX™, and LIPOLASE ULTRA™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g., a special strain of Bacillus licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include GUARDZYME™ (Novozymes A/S).

The enzymatic component(s) may be included in a detergent composition by adding separate additives containing one or more enzymes, or by adding a combined additive comprising all of these enzymes. A detergent additive of the present invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzymatic component(s) of the detergent composition of the present invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzymatic component, in particular the polypeptides having cellobiohydrolase activity of the present invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptides having cellobiohydrolase activity of the present invention may additionally be incorporated in the detergent formulations disclosed in WO 97/07202 which is hereby incorporated as reference.

Signal Peptide

The present invention also relates to nucleic acid constructs comprising a gene encoding a protein, wherein the gene is operably linked to a nucleotide sequence encoding a signal peptide comprising or consisting of amino acids 1 to 17 of SEQ ID NO: 2, wherein the gene is foreign to the nucleotide sequence.

In a preferred aspect, the nucleotide sequence comprises or consists of nucleotides 1 to 51 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Myceliophthora thermophila* CBS 202.75 was used as the source of the gene for a Family 6 polypeptide having cellobiohydrolase activity. *Aspergillus oryzae* JaL355 strain (WO 2002/40694) was used for expression of the *Myceliophthora thermophila* gene encoding the polypeptide having cellobiohydrolase activity.

Media

Minimal medium plates were composed per liter of 6 g of NaNO₃, 0.52 g of KCl, 1.52 g of KH₂PO₄, 1 ml of COVE trace elements solution, 20 g of Noble agar, 20 ml of 50% glucose, 2.5 ml of MgSO₄.7H₂O, and 20 ml of a 0.02% biotin solution.

COVE trace elements solution was composed per liter of 0.04 g of Na₂B₄O₇.10H₂O, 0.4 g of CuSO₄.5H₂O, 1.2 g of FeSO₄.7H₂O, 0.7 g of MnSO₄.H₂O, 0.8 g of Na₂MoO₂.2H₂O, and 10 g of ZnSO₄.7H₂O.

MDU2BP medium was composed per liter of 45 g of maltose, 1 g of MgSO₄.7H₂O, 1 g of NaCl, 2 g of K₂SO₄, 12 g of KH₂PO₄, 7 g of yeast extract, 2 g of urea, and 0.5 ml of AMG trace metals solution; pH 5.0.

AMG trace metals solution was composed per liter of 14.3 g of ZnSO₄.7H₂O, 2.5 g of CuSO₄.5H₂O, 0.5 g of NiCl₂.6H₂O, 13.8 g of FeSO₄.7H₂O, 8.5 g of MnSO₄.7H₂O, and 3 g of citric acid.

YEG medium was composed per liter of 20 g of dextrose and 5 g of yeast extract.

Example 1

*Myceliophthora thermophila* CBS 202.75 Genomic DNA Extraction

*Myceliophthora thermophila* CBS 202.75 was grown in 100 ml of YEG medium in a baffled shake flask at 45° C. and 200 rpm for 2 days. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

Example 2

Isolation of a Full-Length Family 6 Cellobiohydrolase Gene (cel6a) from *Myceliophthora thermophila* CBS 202.75

A full-length Family 6 cellobiohydrolase gene (cel6a) was isolated from *Myceliophthora thermophila* CBS 202.75 using a GENOMEWALKER™ Universal Kit (Clontech Laboratories, Inc., Mountain View, Calif., USA) according to the manufacturer's instructions. Briefly, total genomic DNA from *Myceliophthora thermophila* CBS 202.75 was digested separately with four different restriction enzymes (Dra I, Eco RV, Pvu II, and Stu I) that leave blunt ends. Each batch of digested genomic DNA was then ligated separately to the GENOMEWALKER™ Adaptor (Clontech Laboratories, Inc., Mountain View, Calif., USA) to create four libraries. These libraries were then employed as templates in PCR reactions using two gene-specific primers shown below, one for primary PCR and one for secondary PCR. The primers were designed based on a partial Family 6 cellobiohydrolase gene (cel6a) sequence from *Myceliophthora thermophila* (WO 2004/056981).

```
Primer MtCel6a-R4:
                                    (SEQ ID NO: 3)
5'-ATTGGCAGCCCGGATCTGGGACAGAGTCTG-3'

Pimer MtCel6a-R5:
                                    (SEQ ID NO: 4)
5'-CCGGTCATGCTAGGAATGGCGAGATTGTGG-3'
```

The primary amplifications were composed of 1 µl (approximately 6 ng) of each library as template, 0.4 mM each of dATP, dTTP, dGTP, and dCTP, 10 pmol of Adaptor Primer 1 (Clontech Laboratories, Inc., Mountain View, Calif., USA), 10 pmol of primer MtCel6a-R4, 2 µl of 1× ADVANTAGE® GC-Melt LA Buffer (Clontech Laboratories, Inc., Mountain View, Calif., USA), and 1.25 units of ADVANTAGE® GC Genomic Polymerase Mix (Clontech Laboratories, Inc., Mountain View, Calif., USA) in a final volume of 25 µl. The amplifications were performed using an EPPENDORF® MASTERCYCLER® 5333 (Eppendorf Scientific, Inc., Westbury, N.Y., USA) programmed for pre-denaturing at 94° C. for 1 minute; seven cycles each at a denaturing temperature of 94° C. for 30 seconds; annealing and elongation at 72° C. for 5 minutes; and 32 cycles each at 67° C. for 5 minutes.

The secondary ampliifications were composed of 1 µl of each primary PCR product as template, 0.4 mM each of dATP, dTTP, dGTP, and dCTP, 10 pmol of Adaptor Primer 2 (Clontech Laboratories, Inc., Mountain View, Calif., USA), 10 pmol of primer MtCel6a-R5, 1× ADVANTAGE® GC-Melt LA Buffer, and 1.25 units of ADVANTAGE® GC Genomic Polymerase Mix in a final volume of 25 µl. The amplifications were performed using an EPPENDORF® MASTERCYCLER® 5333 programmed for pre-denaturing at 94° C. for 1 minute; 5 cycles each at a denaturing temperature of 94° C. for 30 seconds; annealing and elongation at 72° C. for 5 minutes; and 20 cycles at 67° C. for 5 minutes.

The reaction products were isolated by 1.0% agarose gel electrophoresis using 40 mM Tris base-20 mM sodium acetate-1 mM disodium EDTA (TAE) buffer where a 3.5 kb product band from the Eco RV library was excised from the gel, purified using a QIAQUICK® Gel Extraction Kit (QIAGEN, Valencia, Calif., USA) according to the manufacturer's instructions, and sequenced.

Example 3

Characterization of the *Myceliophthora thermophila* Genomic Sequence Encoding a Family 6 Cellobiohydrolase DNA sequencing of the 3.5 kb PCR fragment was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, *Journal of Virology Methods* 38: 47-60) and primer walking strategy. The following gene specific primers were used for sequencing:

```
MtCel6a-F2:
                                    (SEQ ID NO: 5)
5'-GCTGTAAACTGCGAATGGGTTCAG-3'

MtCel6a-F3:
                                    (SEQ ID NO: 6)
5'-GGGTCCCACATGCTGCGCCT-3'

MtCel6a-R8:
                                    (SEQ ID NO: 7)
5'-AAAATTCACGAGACGCCGGG-3'
```

Nucleotide sequence data were scrutinized for quality and all sequences were compared to each other with assistance of PHRED/PHRAP software (University of Washington, Seattle, Wash., USA). The 3.5 kb sequence was compared and aligned with a partial Family 6 cellobiohydrolase gene (cel6a) sequence from *Myceliophthora thermophila* (WO 2004/056981).

Figure 1A:
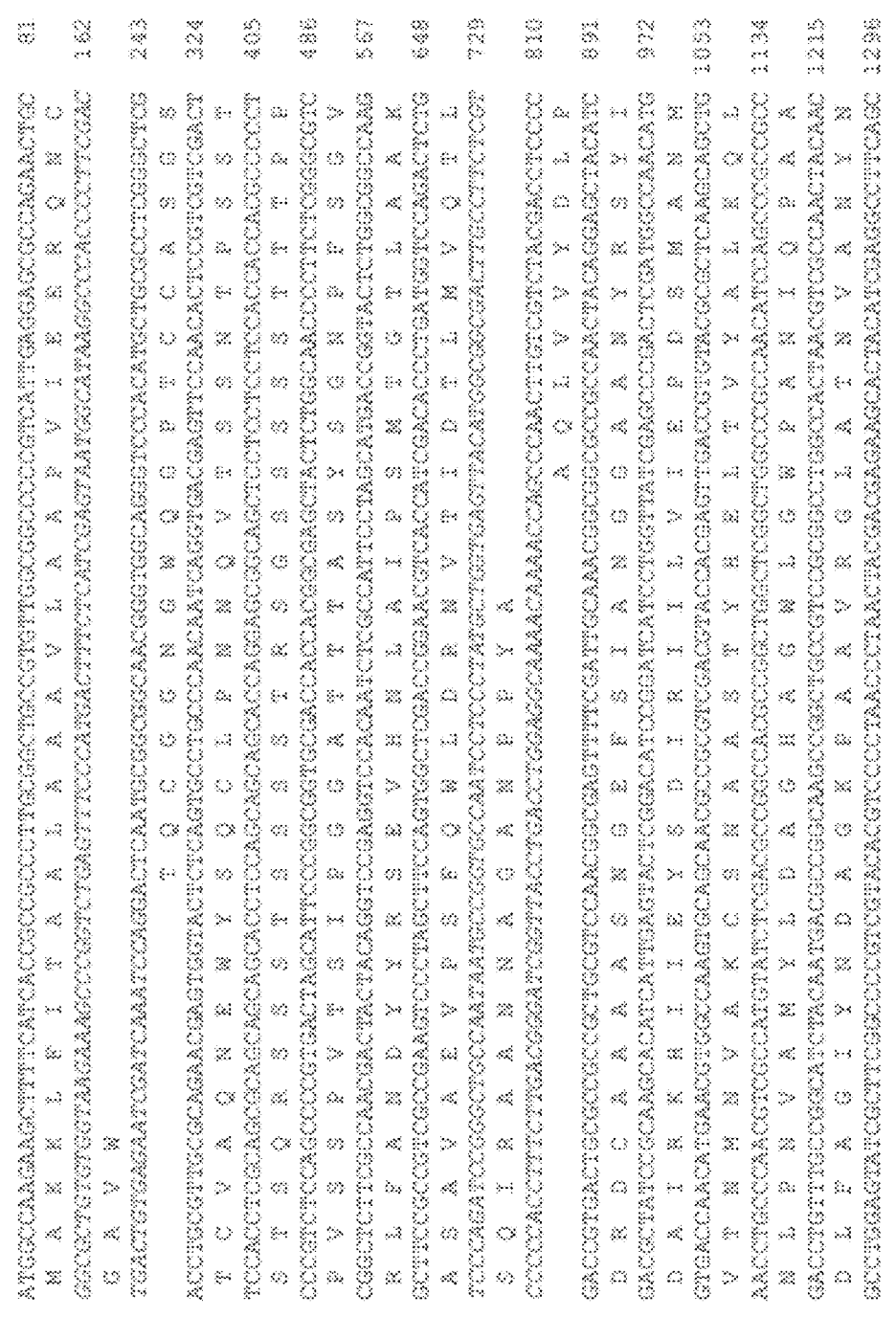
Figure 1B:
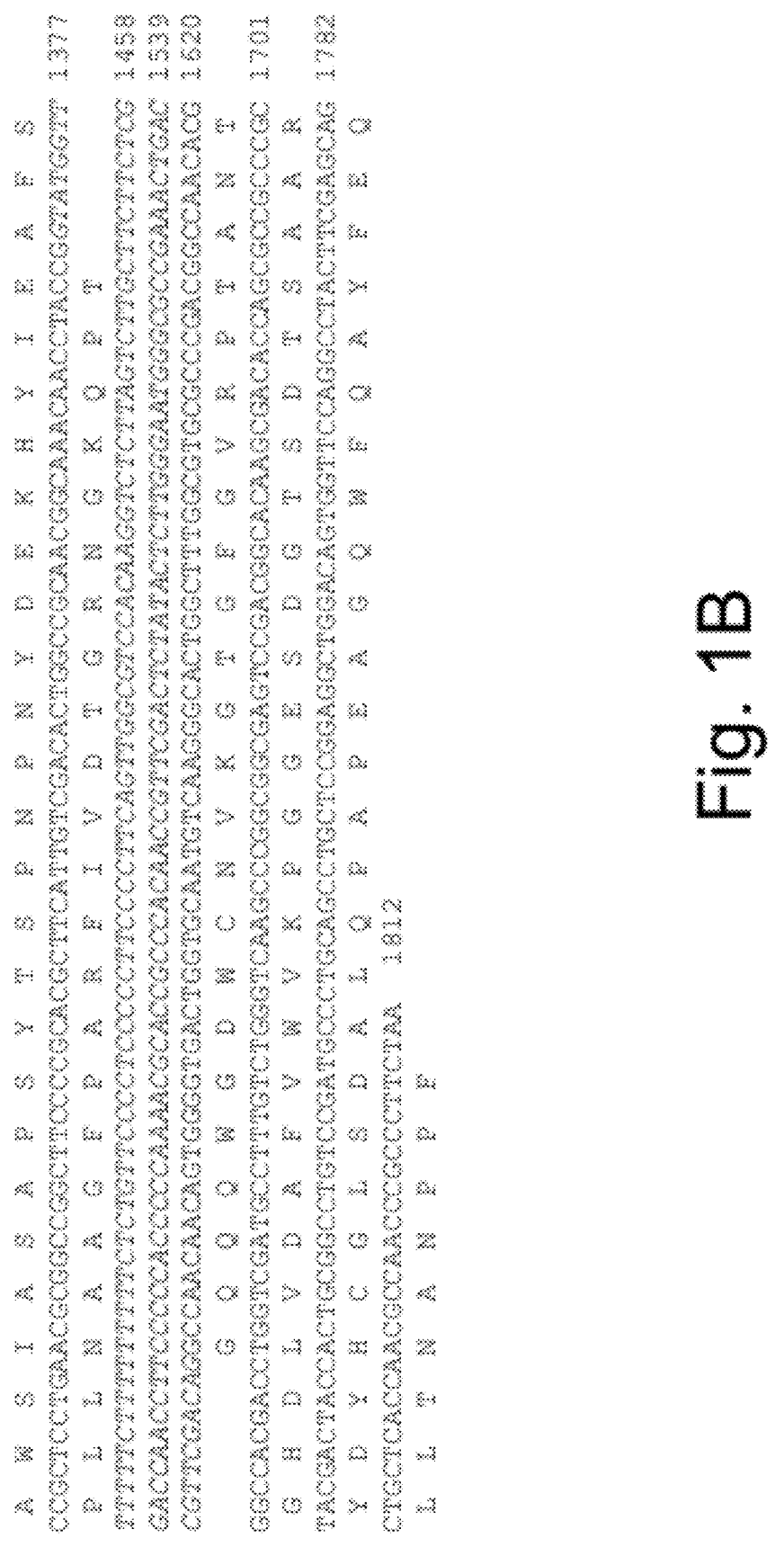

A gene model for the *Myceliophthora thermophila* sequence was constructed based on similarity of the encoded protein to homologous glycoside hydrolase Family 6 proteins from *Thielavia terrestris, Chaetomium thermophilum, Humicola insolens*, and *Trichoderma reesei*. The nucleotide sequence (SEQ ID NO: 1) and deduced amino acid sequence (SEQ ID NO: 2) are shown in FIGS. 1A and 1B. The genomic fragment encodes a polypeptide of 482 amino acids, interrupted by 3 introns of 96, 87, and 180 bp. The % G+C content of the gene and the mature coding sequence are 61.6% and 64%, respectively. Using the SignalP software program (Nielsen et al., 1997, *Protein Engineering* 10:1-6), a signal peptide of 17 residues was predicted. The predicted mature protein contains 465 amino acids with a molecular mass of 49.3 kDa.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Myceliophthora thermophila* gene encoding the CEL6A mature polypeptide having cellobiohydrolase activity shared 78.6% and 77.6% identity (excluding gaps) to the deduced amino acid sequences of two glycoside hydrolase Family 6 proteins from *Chaetomium thermophilum* and *Humicola insolens*, respectively (GeneSeqP accession numbers ADP84824 and AAW44853, respectively).

Example 4

Cloning of the *Myceliophthora thermophila* Cellobiohydrolase Gene (Cel6a) and Construction of an *Aspergillus oryzae* Expression Vector Two synthetic oligonucleotide primers shown below were designed to PCR amplify the *Myceliophthora thermophila* cellobiohydrolase gene from the genomic DNA prepared in Example 1. An InFusion Cloning Kit (BD Biosciences, Palo Alto, Calif., USA) was used to clone the fragment directly into the expression vector pAlLo2 (WO 2004/099228), without the need for restriction digestion and ligation.

```
MtCel6a-F4:
                                         (SEQ ID NO: 8)
5'-ACTGGATTTACCATGGCCAAGAAGCTTTTCATCACC-3'

MtCel6a-R9:
                                         (SEQ ID NO: 9)
5'-TCACCTCTAGTTAATTAATTAGAAGGGCGGGTTGGCGT-3'
```

Bold letters represent coding sequence. The remaining sequence is homologous to the insertion sites of pAlLo2.

Fifty picomoles of each of the primers above were used in a PCR reaction composed of 100 ng of *Myceliophthora thermophila* genomic DNA, 2 μl of 1× ADVANTAGE® GC-Melt LA Buffer, 0.4 mM each of dATP, dTTP, dGTP, and dCTP, and 1.25 units of ADVANTAGE® GC Genomic Polymerase Mix in a final volume of 25 μl. The amplification was performed using an EPPENDORF® MASTERCYCLER® 5333 programmed for 1 cycle at 94° C. for 1 minutes; and 30 cycles each at 94° C. for 30 seconds, 62° C. for 30 seconds, and 72° C. for 2 minutes. The heat block then went to a 4° C. soak cycle.

The reaction products were isolated by 1.0% agarose gel electrophoresis using TAE buffer where a 1842 bp product band was excised from the gel, and purified using a QIAQUICK® Gel Extraction Kit according to the manufacturer's instructions.

Plasmid pAlLo2 (WO 2004/099228) was digested with Nco I and Pac I, isolated by 1.0% agarose gel electrophoresis using TAE buffer, and purified using a QIAQUICK® Gel Extraction Kit according to the manufacturer's instructions.

The gene fragment and the digested vector were ligated together using an InFusion Cloning Kit resulting in pSMai180 (FIG. 2) in which transcription of the cellobiohydrolase gene was under the control of a hybrid of promoters from the genes for *Aspergillus niger* neutral alpha-amylase and *Aspergillus oryzae* triose phosphate isomerase (NA2-tpi promoter). The ligation reaction (50 μl) was composed of 1× InFusion Buffer (BD Biosciences, Palo Alto, Calif., USA), 1×BSA (BD Biosciences, Palo Alto, Calif., USA), 1 μl of Infusion enzyme (diluted 1:10) (BD Biosciences, Palo Alto, Calif., USA), 100 ng of pAlLo2 digested with Nco I and Pac I, and 50 ng of the *Myceliophthora thermophila* cel6a purified PCR product. The reaction was incubated at room temperature for 30 minutes. One μl of the reaction was used to transform *E. coli* XL10 SOLOPACK® Gold Supercompetent cells (Stratagene, La Jolla, Calif., USA). An *E. coli* transformant containing pSMai180 was detected by restriction digestion and plasmid DNA was prepared using a BIOROBOT® 9600 (QIAGEN Inc., Valencia, Calif., USA). The *Myceliophthora thermophila* cel6a insert in pSMai180 was confirmed by DNA sequencing.

The same 1842 bp PCR fragment was cloned into pCR02.1—TOPO vector (Invitrogen, Carlsbad, Calif., USA) using a TOPO TA CLONING® Kit, to generate pSMai182 (FIG. 2). The *Myceliophthora thermophila* cel6a insert in pSMai182 was confirmed by DNA sequencing. *E. coli* pSMai182 was deposited with the Agricultural Research Service Patent Culture Collection, Northern Regional Research Center, Peoria, Ill., USA, on Sep. 6, 2007.

Example 6

Expression of the *Myceliophthora thermophila* Family 6 Cellobiohydrolase cel6a Gene in *Aspergillus oryzae* JaL355

*Aspergillus oryzae* JaL355 (WO 2002/40694) protoplasts were prepared according to the method of Christensen et al., 1988, *Bio/Technology* 6: 1419-1422. Three μg of pSMai180 were used to transform *Aspergillus oryzae* JaL355.

The transformation of *Aspergillus oryzae* JaL355 with pSMai180 yielded about 50 transformants. Twenty transformants were isolated to individual Minimal medium plates.

Confluent Minimal Medium plates of the 20 transformants were washed with 5 ml of 0.01% TWEEN® 20 and inoculated separately into 25 ml of MDU2BP medium in 125 ml glass shake flasks and incubated at 34° C., 250 rpm. After 5 days incubation, 5 μl of supernatant from each culture were analyzed on CRITERION® Tris-HCl gels (Bio-Rad Laboratories, Hercules, Calif., USA) with a CRITERION® Cell (Bio-Rad Laboratories, Hercules, Calif., USA), according to the manufacturer's instructions. The resulting gel was stained with BIO-SAFE™ Coomassie Stain (Bio-Rad Laboratories, Hercules, Calif., USA). SDS-PAGE profiles of the cultures showed that the majority of the transformants had a major band of approximately 70 kDa.

A confluent plate of one transformant, designated transformant 14, was washed with 10 ml of 0.01% TWEEN® 20 and inoculated into a 2 liter Fernbach containing 500 ml of MDU2BP medium to generate broth for characterization of the enzyme. The culture was harvested on day 5 and filtered using a 0.22 μm EXPRESS™ Plus Membrane (Millipore, Bedford, Mass., USA).

Example 7

Characterization of *Myceliophthora thermophila* CEL6A Cellobiohydrolase

Corn stover was pretreated at the U.S. Department of Energy National Renewable Energy Laboratory (NREL), Boulder, Colo., USA, using dilute sulfuric acid. The following conditions were used for the pretreatment: 0.048 g sulfuric acid per g dry biomass at 190° C. and 25% w/w dry solids for around 1 minute. The water-insoluble solids in the pretreated corn stover (PCS) contained 53.2% cellulose, 3.6% hemicellulose and 29.8% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. Prior to enzymatic hydrolysis, the PCS was washed with a large volume of distilled water until the pH was higher than 4.0, then sieved through 100-mash sieve, and finally autoclaved at 121° C. for 30 minutes. The dry content of the washed and sieved PCS was found to be 6.54%.

Shake flask broth of *Myceliophthora thermophila* CEL6A cellobiohydrolase prepared as described in Example 6 was desalted using an ECONO-PAC® 10DG column (Bio-Rad Laboratories, Inc., Hercules, Calif., USA). Protein concentration was determined using a Microplate BCA™ Protein Assay Kit (Pierce, Rockford, Ill., USA).

*Trichoderma reesei* CEL7B endoglucanase I was cloned and expressed in *Aspergillus oryzae* JaL250 as described in WO 2005/067531. Protein concentration was determined using a Microplate BCA™ Protein Assay Kit. The *Trichoderma reesei* CEL7B endoglucanase I was desalted and buffer exchanged in 150 mM NaCl-20 mM sodium acetate pH 5.0 using a HIPREP® 26/10 Desalting Column (GE Healthcare Life Sciences, Piscataway, N.J., USA) according to the manufacturer's instructions.

*Aspergillus oryzae* Cel3A beta-glucosidase was recombinantly prepared as described in WO 2004/099228, and purified as described by Langston et al., 2006, *Biochim. Biophys. Acta Proteins Proteomics* 1764: 972-978. Protein concentration was determined using a Microplate BCA™ Protein Assay Kit. *Penicillium brasilianum* IBT 20888 Cel3A beta-glucosidase was recombinantly produced and desalted using a HIPREP® 26/10 Desalting Column, as above, and further purified with a Mono Q® column using an AKTA FPLC System (GE Healthcare Life Sciences, Piscataway, N.J., USA) according to the manufacturer's instructions.

*Trichoderma reesei* CEL6A cellobiohydrolase gene was isolated from *Trichoderma reesei* RutC30 as described in WO 2005/056772. The *Trichoderma reesei* CEL6A cellobiohydrolase gene was expressed in *Fusarium venenatum* using pEJG61 as an expression vector according to the procedures described in U.S. Patent Application 20060156437. Fermentation was performed as described in U.S. Patent Application 20060156437. Protein concentration was determined using a Microplate BCA™ Protein Assay Kit. *Trichoderma reesei* CEL6A cellobiohydrolase was desalted and buffer-exchanged into 20 mM sodium acetate-150 mM NaCl pH 5.0 using a HIPREP® 26/10 Desalting column according to the manufacturer's instructions.

Hydrolysis of PCS was performed in 96-deep-well plates (Axygen Scientific, Union City, Calif., USA) sealed by a plate sealer (ALPS-300, Abgene, Epsom, UK), with a total reaction volume of 1.0 ml. To test the activity of *Myceliophthora thermophila* cellobiohydrolase, PCS was loaded at 1 mg of cellobiohydrolase per g cellulose, together with 0.5 mg of *Aspergillus oryzae* beta-glucosidase per g cellulose. *Trichoderma reesei* CEL6A cellobiohydrolase (1 mg per g cellulose) together with *Aspergillus oryzae* beta-glucosidase (0.5 mg per g cellulose) were used as a control for comparison to the *Myceliophthora thermophila* CEL6A cellobiohydrolase. PCS hydrolysis was performed at pH 5.0, 50° C. in a TS Autoflow $CO_2$ Jacketed Incubator (Fisher Scientific, Pittsburgh, Pa., USA). Reactions were run in triplicates and aliquots were taken during the course of hydrolysis. PCS hydrolysis reactions were stopped by mixing a 20 μl aliquot of each hydrolyzate with 180 μl of 0.1 M NaOH (stop reagent). Appropriate serial dilutions were generated for each sample and the reducing sugar content determined using a para-hydroxybenzoic acid hydrazide (PHBAH, Sigma, St. Louis, Mo., USA) assay adapted to a 96 well microplate format. A 100 μl aliquot of an appropriately diluted sample was placed in a 96 well conical bottomed microplate. Reactions were initiated by adding 50 μl of 1.5% (w/v) PHBAH in 2% NaOH to each well. Plates were heated uncovered at 95° C. for 10 minutes, after which 50 μl of distilled water was added to each well. A 100 μl aliquot from each well was transferred to a flat bottomed 96 well plate and the absorbance at 410 nm was measured using a SPECTRAMAX® Microplate Reader (Molecular Devices, Sunnyvale, Calif., USA). Glucose standards (0.1-0.0125 mg/ml diluted with 0.4% sodium hydroxide) were used to prepare a standard curve to translate the obtained $A_{410\ nm}$ values into glucose equivalents. The resultant equivalents were used to calculate the percentage of PCS cellulose conversion for each reaction.

The degree of cellulose conversion to reducing sugar (% conversion) was calculated using the following equation:

$$\%\ \text{Conversion} = RS_{(mg/ml)} \times 100 \times 162 / (\text{cellulose}_{(mg/ml)} \times 180) = RS_{(mg/ml)} \times 100 / (\text{cellulose}_{(mg/ml)} \times 1.111)$$

In this equation, RS is the concentration of reducing sugar in solution measured in glucose equivalents (mg/ml), and the factor 1.111 reflects the weight gain in converting cellulose to glucose.

The results are summarized in Table 1. *Myceliophthora thermophila* CEL6A cellobiohydrolase had similar or slightly higher activity on PCS than *Trichoderma reesei* CEL6A cellobiohydrolase in the presence of *Aspergillus oryzae* beta-glucosidase.

TABLE 1

Cellulose conversion by *Myceliophthora thermophila* CEL6A cellobiohydrolase or *Trichoderma reesei* CEL6A cellobiohydrolase plus *Aspergillus oryzae* beta-glucosidase

| Test # | Enzyme Name | Loading, mg/g cellulose | Conversion at 65 hours, % |
|---|---|---|---|
| 1 | *M. thermophila* CBH + *A. oryzae* beta-glucosidase | 1 + 0.5 | 5.0 |
| 2 | *T. reesei* CBH + *A. oryzae* beta-glucosidase | 1 + 0.5 | 3.7 |

Desalted *Myceliophthora thermophila* Cel6A was further purified through a PHENYL SUPEROSE® HR 16/10 column (GE Healthcare Life Sciences, Piscataway, N.J., USA) using an AKTA FPLC System. SDS-PAGE of the sample showed that it was at least 90% pure. Other enzymes used below were also further purified, as above, using an AKTA FPLC System, with purity higher than 90%.

Hydrolysis of PCS (40 g/L in reaction) was conducted in 96-deep-well plates and sealed as described above, with a total reaction volume of 1.0 ml. *Myceliophthora thermophila* Cel6A cellobiohydrolase, in comparison with *Trichoderma reesei* Cel6A cellobiohydrolase, were tested in PCS hydrolysis using artificial enzyme mixtures at pH 5, 50 and 55° C. (TS Autoflow $CO_2$ Jacketed Incubator). The enzyme mixtures were composed of *Trichoderma reesei* Cel7B endoglucanase (2 mg/g cellulose), *Penicillium brasilianum* GH3A beta-glucosidase (0.3 mg/g cellulose), and either *Myceliophthora thermophila* Cel6A cellobiohydrolase or *Trichoderma reesei* Cel6A cellobiohydrolase, (2 mg/g cellulose). PCS hydrolysis reactions were stopped by mixing a 20 µl aliquot of each hydrolyzate with 180 µl of 0.1 M NaOH (stop reagent). Analysis of the hydrolysis reactions and calculations were performed as described above. Cellulose conversion results are summarized in Table 2.

TABLE 2

Cellulose conversion by *Trichoderma reesei* Cel7B endoglucanase (2 mg/g cellulose), *Penicillium brasilianum* GH3A beta-glucosidase (0.3 mg/g cellulose), and either *Myceliophthora thermophila* Cel6A or *Trichoderma reesei* Cel6A cellobiohydrolase (2 mg/g cellulose), pH 5, 50 and 55° C.

| Test # | Enzyme Name (mg/g cellulose) | Temperature, ° C. | Conversion at 72 h, % |
|---|---|---|---|
| 1 | T. reesei Cel7B endoglucanase (2) + P. brasilianum GH3A beta-glucosidase (0.3) + M. thermophila Cel6A cellobiohydrolase (2) | 50 | 22.5 |
| 2 | T. reesei Cel7B endoglucanase (2) + P. brasilianum GH3A beta-glucosidase (0.3) + T. reesei Cel6A cellobiohydrolase (2) | 50 | 19.6 |
| 3 | T. reesei Cel7B endoglucanase (2) + P. brasilianum GH3A beta-glucosidase (0.3) + M. thermophila Cel6A cellobiohydrolase (2) | 55 | 25.9 |
| 4 | T. reesei Cel7B endoglucanase (2) + P. brasilianum GH3A (0.3) + T. reesei Cel6A cellobiohydrolase (2) | 55 | 18.2 |

Table 1 showed that the *Myceliophthora thermophila* 6A cellobiohydrolase outperformed the *Trichoderma reesei* 6A cellobiohydrolase in PCS hydrolysis at both 50 and 55° C., and especially at 55° C.

Deposit of Biological Material

The following biological material has been deposited under the terms of the Budapest Treaty with the Agricultural Research Service Patent Culture Collection (NRRL), Northern Regional Research Center, 1815 University Street, Peoria, Ill., USA, and given the following accession number:

| Deposit | Accession Number | Date of Deposit |
|---|---|---|
| E. coli pSMai182 | NRRL B-50059 | Sep. 6, 2007 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method of producing a mutant cell, comprising disrupting or deleting a nucleotide sequence encoding a polypeptide having cellobiohydrolase activity in a parent *Myceliophthora thermophila* cell, which results in the mutant producing less of the polypeptide than the parent *Myceliophthora thermophila* cell, wherein the polypeptide having cellobiohydrolase activity is selected from the group consisting of:

(a) a polypeptide having cellobiohydrolase activity comprising an amino acid sequence having at least 99% identity to amino acids 18 to 842 of SEQ ID NO: 2; and (b) a polypeptide having cellobiohydrolase activity comprising amino acids 18 to 482 of SEQ ID NO: 2.

2. The method of claim 1, wherein the polypeptide is encoded by the polynucleotide contained in plasmid pSMai182 which is contained in *E. coli* NRRL B-50059.

3. A mutant cell, comprising a disruption or deletion of a nucleotide sequence encoding a polypeptide having cellobiohydrolase activity in a parent *Myceliophthora thermophila* cell, wherein the mutant produces less of the polypeptide than the parent *Myceliophthora thermophila* cell, and wherein the polypeptide having cellobiohydrolase activity is selected from the group consisting of:

(a) a polypeptide having cellobiohydrolase activity comprising an amino acid sequence having at least 99% identity to amino acids 18 to 842 of SEQ ID NO: 2; and (b) a polypeptide having cellobiohydrolase activity comprising amino acids 18 to 482 of SEQ ID NO: 2.

4. The mutant cell of claim 3, wherein the polypeptide is encoded by the polynucleotide contained in plasmid pSMai182 which is contained in *E. coli* NRRL B-50059.

5. The mutant cell of claim 3, further comprising an expression vector for a protein.

6. The mutant cell of claim 5, wherein the protein is a native protein.

7. The mutant cell of claim 5, wherein the protein is a heterologous protein.

8. A method of producing a protein, comprising: (a) cultivating the mutant cell of claim 5 under conditions conducive for production of the protein; and (b) recovering the protein.

\* \* \* \* \*

SEQUENCE LISTING

```
<160> NUMBER OF SEQ ID NOS: 9

<210> SEQ ID NO 1
<211> LENGTH: 1812
<212> TYPE: DNA
<213> ORGANISM: Myceliophthora thermophila

<400> SEQUENCE: 1
atggccaaga agcttttcat caccgccgcc cttgcggctg ccgtgttggc ggcccccgtc      60
attgaggagc gccagaactg cggcgctgtg tggtaagaaa gcccggtctg agtttcccat     120
gactttctca tcgagtaatg gcataaggcc caccccttcg actgactgtg agaatcgatc     180
aaatccagga ctcaatgcgg cggcaacggg tggcagggtc ccacatgctg cgcctcgggc     240
tcgacctgcg ttgcgcagaa cgagtggtac tctcagtgcc tgcccaacaa tcaggtgacg     300
```

-continued

```
agttccaaca ctccgtcgtc gacttccacc tcgcagcgca gcagcagcac ctccagcagc    360
agcaccagga gcggcagctc ctcctcctcc accaccacgc ccctcccgt ctccagcccc     420
gtgactagca ttcccggcgg tgcgaccacc acggcgagct actctggcaa cccttctcg     480
ggcgtccggc tcttcgccaa cgactactac aggtccgagg tccacaatct cgccattcct    540
agcatgaccg gtactctggc ggccaaggct tccgccgtcg ccgaagtccc tagcttccag    600
tggctcgacc ggaacgtcac catcgacacc ctgatggtcc agactctgtc ccagatccgg    660
gctgccaata tgccggtgc caatcctccc tatgctggtg agttacatgg cggcgacttg     720
ccttctcgtc ccccaccttt cttgacggga tcggttacct gacctggagg caaaacaaaa    780
ccagcccaac ttgtcgtcta cgacctcccc gaccgtgact gcgccgccgc tgcgtccaac    840
ggcgagtttt cgattgcaaa cggcggcgcc gccaactaca ggagctacat cgacgctatc    900
cgcaagcaca tcattgagta ctcggacatc cggatcatcc tggttatcga gcccgactcg    960
atggccaaca tggtgaccaa catgaacgtg ccaagtgca gcaacgccgc gtcgacgtac    1020
cacgagttga ccgtgtacgc gctcaagcag ctgaacctgc caacgtcgc catgtatctc    1080
gacgccggcc acgccggctg gctcggctgg cccgccaaca tccagcccgc cgccgacctg    1140
tttgccggca tctacaatga cgccggcaag ccggctgccg tccgcggcct ggccactaac    1200
gtcgccaact acaacgcctg gagtatcgct tcggccccgt cgtacacgtc ccctaaccct    1260
aactacgacg agaagcacta catcgaggcc ttcagcccgc tcctgaacgc ggccggcttc    1320
cccgcacgct tcattgtcga cactggccgc aacggcaaac aacctaccgg tatggttttt    1380
ttcttttttt ttctctgttc ccctccccct tccccttcag ttggcgtcca caggtctct    1440
tagtcttgct tcttctcgga ccaaccttcc cccaccccca aaacgcaccg cccacaaccg    1500
ttcgactcta tactcttggg aatgggcgcc gaaactgacc gttcgacagg ccaacaacag    1560
tggggtgact ggtgcaatgt caagggcact ggctttggcg tgcgcccgac ggccaacacg    1620
ggccacgacc tggtcgatgc ctttgtctgg gtcaagcccg gcggcgagtc cgacggcaca    1680
agcgacacca gcgccgcccg ctacgactac cactgcggcc tgtccgatgc cctgcagcct    1740
gctccggagg ctggacagtg gttccaggcc tacttcgagc agctgctcac caacgccaac    1800
ccgcccttct aa                                                       1812
```

<210> SEQ ID NO 2
<211> LENGTH: 482
<212> TYPE: PRT
<213> ORGANISM: Myceliophthora thermophila

<400> SEQUENCE: 2

```
Met Ala Lys Lys Leu Phe Ile Thr Ala Ala Leu Ala Ala Ala Val Leu
  1               5                  10                  15

Ala Ala Pro Val Ile Glu Glu Arg Gln Asn Cys Gly Ala Val Trp Thr
                 20                  25                  30

Gln Cys Gly Gly Asn Gly Trp Gln Gly Pro Thr Cys Cys Ala Ser Gly
             35                  40                  45

Ser Thr Cys Val Ala Gln Asn Glu Trp Tyr Ser Gln Cys Leu Pro Asn
         50                  55                  60

Asn Gln Val Thr Ser Ser Asn Thr Pro Ser Ser Thr Ser Thr Ser Gln
     65                  70                  75                  80

Arg Ser Ser Ser Thr Ser Ser Ser Thr Arg Ser Gly Ser Ser Ser
                 85                  90                  95

Ser Ser Thr Thr Thr Pro Pro Pro Val Ser Ser Pro Val Thr Ser Ile
             100                 105                 110
```

Pro Gly Gly Ala Thr Thr Ala Ser Tyr Ser Gly Asn Pro Phe Ser
            115                 120                 125

Gly Val Arg Leu Phe Ala Asn Asp Tyr Tyr Arg Ser Glu Val His Asn
        130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
                180                 185                 190

Ala Gly Ala Asn Pro Pro Tyr Ala Ala Gln Leu Val Val Tyr Asp Leu
            195                 200                 205

Pro Asp Arg Asp Cys Ala Ala Ala Ser Asn Gly Glu Phe Ser Ile
        210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
                260                 265                 270

Ser Asn Ala Ala Ser Thr Tyr His Glu Leu Thr Val Tyr Ala Leu Lys
            275                 280                 285

Gln Leu Asn Leu Pro Asn Val Ala Met Tyr Leu Asp Ala Gly His Ala
        290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
                340                 345                 350

Ser Tyr Thr Ser Pro Asn Pro Asn Tyr Asp Glu Lys His Tyr Ile Glu
            355                 360                 365

Ala Phe Ser Pro Leu Leu Asn Ala Ala Gly Phe Pro Ala Arg Phe Ile
        370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Asp Leu Val Asp Ala Phe Val Trp Val Lys Pro
                420                 425                 430

Gly Gly Glu Ser Asp Gly Thr Ser Asp Thr Ser Ala Ala Arg Tyr Asp
            435                 440                 445

Tyr His Cys Gly Leu Ser Asp Ala Leu Gln Pro Ala Pro Glu Ala Gly
        450                 455                 460

Gln Trp Phe Gln Ala Tyr Phe Glu Gln Leu Leu Thr Asn Ala Asn Pro
465                 470                 475                 480

Pro Phe

<210> SEQ ID NO 3
<211> LENGTH: 30
<212> TYPE: DNA
<213> ORGANISM: Myceliophthora thermophila

<400> SEQUENCE: 3

-continued

```
attggcagcc cggatctggg acagagtctg                                30

<210> SEQ ID NO 4
<211> LENGTH: 30
<212> TYPE: DNA
<213> ORGANISM: Myceliophthora thermophila

<400> SEQUENCE: 4
ccggtcatgc taggaatggc gagattgtgg                                30

<210> SEQ ID NO 5
<211> LENGTH: 24
<212> TYPE: DNA
<213> ORGANISM: Myceliophthora thermophila

<400> SEQUENCE: 5
gctgtaaact gcgaatgggt tcag                                      24

<210> SEQ ID NO 6
<211> LENGTH: 20
<212> TYPE: DNA
<213> ORGANISM: Myceliophthora thermophila

<400> SEQUENCE: 6
gggtcccaca tgctgcgcct                                           20

<210> SEQ ID NO 7
<211> LENGTH: 20
<212> TYPE: DNA
<213> ORGANISM: Myceliophthora thermophila

<400> SEQUENCE: 7
aaaattcacg agacgccggg                                           20

<210> SEQ ID NO 8
<211> LENGTH: 36
<212> TYPE: DNA
<213> ORGANISM: Myceliophthora thermophila

<400> SEQUENCE: 8
actggattta ccatggccaa gaagcttttc atcacc                         36

<210> SEQ ID NO 9
<211> LENGTH: 38
<212> TYPE: DNA
<213> ORGANISM: Myceliophthora thermophila

<400> SEQUENCE: 9
tcacctctag ttaattaatt agaagggcgg gttggcgt                       38
```